(12) United States Patent
Bille

(10) Patent No.: US 8,377,048 B2
(45) Date of Patent: Feb. 19, 2013

(54) MINIMIZING THE SIDE-EFFECTS OF REFRACTIVE CORRECTIONS USING STATISTICALLY DETERMINED IRREGULARITIES IN INTRASTROMAL INCISIONS

(75) Inventor: Josef F. Bille, Heidelberg (DE)

(73) Assignee: Technolas Perfect Vision GmbH, Munich (DE)

(*) Notice: Subject to any disclaimer, the term of this patent is extended or adjusted under 35 U.S.C. 154(b) by 1081 days.

(21) Appl. No.: 12/349,257

(22) Filed: Jan. 6, 2009

(65) Prior Publication Data
US 2010/0174274 A1    Jul. 8, 2010

(51) Int. Cl.
*A61B 18/18* (2006.01)
(52) U.S. Cl. .................................................. 606/5
(58) Field of Classification Search .............. 128/898; 606/4–6; 623/4.1–6.64, 905–907
See application file for complete search history.

(56) References Cited

U.S. PATENT DOCUMENTS

| | | | |
|---|---|---|---|
| 4,309,998 A | 1/1982 | Aron nee Rosa et al. | |
| 4,391,275 A | 7/1983 | Fankhauser et al. | |
| 4,669,466 A | 6/1987 | L'Esperance | |
| 4,718,418 A | 1/1988 | L'Esperance, Jr. | |
| 4,721,379 A | 1/1988 | L'Esperance | |
| 4,732,148 A | 3/1988 | L'Esperance, Jr. | |
| 4,770,172 A | 9/1988 | L'Esperance, Jr. | |
| 4,887,592 A | 12/1989 | Loertscher | |
| 4,907,586 A | 3/1990 | Bille et al. | |
| 4,941,093 A | 7/1990 | Marshall et al. | |
| 4,988,348 A | 1/1991 | Bille | |
| 5,549,632 A | 8/1996 | Lai | |
| 5,984,916 A | 11/1999 | Lai | |
| 5,993,438 A | 11/1999 | Juhasz et al. | |
| 6,110,166 A | 8/2000 | Juhasz | |
| 6,325,792 B1 | 12/2001 | Swinger et al. | |
| 6,610,051 B2 | 8/2003 | Bille | |
| 6,648,877 B1* | 11/2003 | Juhasz et al. | 606/5 |
| 2004/0044355 A1 | 3/2004 | Nevyas | |
| 2006/0106372 A1* | 5/2006 | Kuhn et al. | 606/5 |
| 2008/0039825 A1* | 2/2008 | Lai | 606/5 |
| 2008/0306573 A1* | 12/2008 | Campin et al. | 607/89 |
| 2008/0319464 A1 | 12/2008 | Bischoff et al. | |

* cited by examiner

*Primary Examiner* — Ryan Severson
*Assistant Examiner* — David Eastwood
(74) *Attorney, Agent, or Firm* — Nydegger & Associates

(57) ABSTRACT

A system and method for minimizing adverse visual effects that may be introduced during laser refractive surgery, requires making laser incisions into stromal tissue in a predetermined manner. Specifically, a plurality of irregular incisions are statistically distributed in the stroma in a manner that causes them to be visually elusive, and thereby minimize their adverse visual effects. The incisions must, however, still accomplish their intended surgical purpose of weakening the stroma in a predetermined manner. To do this, each irregular incision has a width of arc length $d\theta_m$, a length $dz_l$ and a characteristic radial distance $dr_n$ from the visual axis of the eye. Values for $d\theta_m$, $dz_l$ and $dr_n$ are established using a random number generator.

15 Claims, 2 Drawing Sheets

MINIMIZING THE SIDE-EFFECTS OF REFRACTIVE CORRECTIONS USING STATISTICALLY DETERMINED IRREGULARITIES IN INTRASTROMAL INCISIONS

FIELD OF THE INVENTION

The present invention pertains generally to systems and methods that are useful for altering the refractive properties of a transparent material. More specifically, the present invention pertains to systems and methods that weaken stromal tissue with a laser beam to correct vision defects of an eye. The present invention is particularly, but not exclusively, useful as a system and method for weakening stromal tissue with laser incisions that are statistically distributed to thereby become visually elusive for minimizing adverse visual side effects that would otherwise be introduced by incisions in the stroma.

BACKGROUND OF THE INVENTION

PresbyLASIK is an excimer laser based method that is used to achieve a multifocal cornea that restores near vision in presbyopic patients. PresbyLASIK is also sometimes called multifocal LASIK because it works on principles virtually identical to the artificial multifocal lenses that provide vision correction for presbyopes, especially presbyopic cataract patients. Essentially, there are two types of presbyLASIK procedures. One is central presbyLASIK wherein a central disk is created for near vision and a peripheral ring is established for distance vision. The other is peripheral presbyLASIK wherein a central disk is created for distance vision and a mid-peripheral ring is created for near vision. It has been shown that the visual results of both types of presbyLASIK procedures compare favorably to the best pseudoaccommodation that could be theoretically achieved using multifocal refractive intraocular lenses. In these LASIK cases, however, there is still the possibility of introducing uncertainties that may compromise the final refractive outcome.

A recently presented procedure for introducing refractive corrections (e.g. the correction of presbyopia) into the cornea of an eye, without LASIK, involves the weakening of tissue in the stroma Specifically, such a procedure is disclosed in U.S. patent application Ser. No. 11/958,202 for an invention entitled "Method for Intrastromal Refractive Surgery," (hereinafter the "'202 Appln") which is assigned to the same assignee as the present invention As disclosed in the '202 Appln, the weakening of stromal tissue is accomplished using a pulsed femtosecond laser beam to create incisions in the stroma It can happen in a small number of cases, however, that these incisions may introduce annoying side-effects in night-vision (e g Halos, ring-patterns around bright light sources) Further, annoying side-effects may result inherently due to the multifocality of the reshaped cornea In any event, the unwanted side-effects are preferably overcome via neuro-adaptive suppression In one of its aspects, neuro-adaptive suppression involves having the brain effectively ignore a visual perception For example, it can be demonstrated that a plethora of irregularities (e g stromal incisions) may be presented in a manner that will visually disguise an underlying regularity Insofar as an ophthalmic laser procedure is concerned, such a neuro-adaptive suppression may be very advantageous In particular, this will be so if the collective irregularities simultaneously accomplish a two-fold purpose For one, a pattern of collective irregularities must accomplish the same refractive correction that would otherwise be obtained by the underlying regularity alone For another, the pattern of irregularities needs to be visually illusive (i e obfuscate the underlying regularity), and thereby minimize any annoying visual side-effects (e g Halos) that might otherwise arise In light of the above, it is an object of the present invention to provide a system and method for minimizing visual side-effects of a refractive surgical procedure that achieves a desired refractive correction with a pseudo-random pattern of irregular stromal incisions Another object of the present invention is to create a pseudo-random pattern of irregular stromal incisions, based on a statistical distribution, for correcting a vision defect with minimal residual side-effects Still another object of the present invention is to provide a system and method for minimizing visual side-effects of a refractive surgical procedure that is simple to use, relatively easy to manufacture, and comparatively cost effective.

SUMMARY OF THE INVENTION

In accordance with the present invention a system and method are provided to surgically correct vision defects in an eye. For this purpose, the present invention envisions creating incisions in the stroma of the eye that alter its biomechanical stress distributions. Specifically, with these incisions, the stroma is structurally altered (i.e. weakened or softened) so it will respond to Intra-Ocular Pressure (IOP), and consequently reshape the cornea to achieve a desired refractive correction. Along with the refractive correction, however, it can happen that annoying visual side effects may also be introduced.

To minimize or eliminate any adverse, visual side effects that may result from a refractive surgical procedure as described above, the present invention effectively obfuscates any regularity in the incisions. To do this, the present invention creates a plurality of irregular incisions within the stroma in a pseudo-random pattern. Further, this pseudo-random pattern is based on a statistical distribution so that the irregular incisions serve a dual purpose. For one, the pattern of irregular incisions becomes visually elusive, to thereby minimize any annoying side effects. For another, the plurality of incisions effectively accomplishes the redistribution of biomechanical stresses necessary to achieve the desired optical correction.

For the methods of the present invention, the desired optical correction must first be diagnosed and defined. Next, an appropriate change for biomechanical stresses within the stroma must be identified. Once this is done, a statistical distribution for the structural alterations (i.e. change in biomechanical stress distributions) is determined.

During actual surgery, a plurality of irregular incisions is created in the stroma. Importantly, each irregular incision is sized and located in accordance with the statistical distribution so that the plurality of incisions becomes visually elusive and structurally effective. To do this, each irregular incision is defined relative to the visual axis and to the anterior surface of the eye. Specifically, each irregular incision is defined by a unique length "dz" that is measured along a line perpendicular to the anterior surface of the eye, and by an arc length "dθ" (i.e. incision width) that is measured along an azimuthal arc centered on the visual axis of the eye. Further, each irregular incision is located at a unique distance from the visual axis. This distance is characterized by a radial increment "dr".

In detail, the arc width $d\theta_m$ for an irregular incision is in a range between approximately 8° and 12°; wherein m=1→36, and $\Sigma d\theta_m = 360°$. Further, all incisions having a same $d\theta_m$ will also have a same length $dz_t$, with an overlap Δ. Preferably;

I=1→10, with each $dz_I$ is in a range of 30 μm to 50 μm, and Δ<approximately 10 μm. Also, the irregular incisions having a same $dθ_m$ are each located by an incremental radial distance $dr_n$; wherein n=1→5, $dr_I$>1 mm and $Σdr_n$<approximately 2 mm. Values for $dθ_m$, $dz_I$ and $dr_n$ are established by using a random number generator.

Within the general parameters set forth above, it is to be appreciated that the statistical distribution should strive for the highest amount of entropy (i.e. be as evenly distributed as possible). Accordingly, to ensure continued biomechanical efficiency, the distance $dr_n$ for an irregular incision having a particular $dθ_m$ is preferably established to be within a predetermined radial distance from the irregular incisions having a respective $dr_n$ (i.e. "n" is the same) in an adjacent arc $dθ_{m+1}$, and in the oppositely adjacent arc $dθ_{m-1}$. Further, to avoid adverse LIOB consequences, within a same arc $dθ_m$, the distance between an irregular incision with radial distance drn and one with $dr_{n+1}$, is preferably greater than approximately 50 μm.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
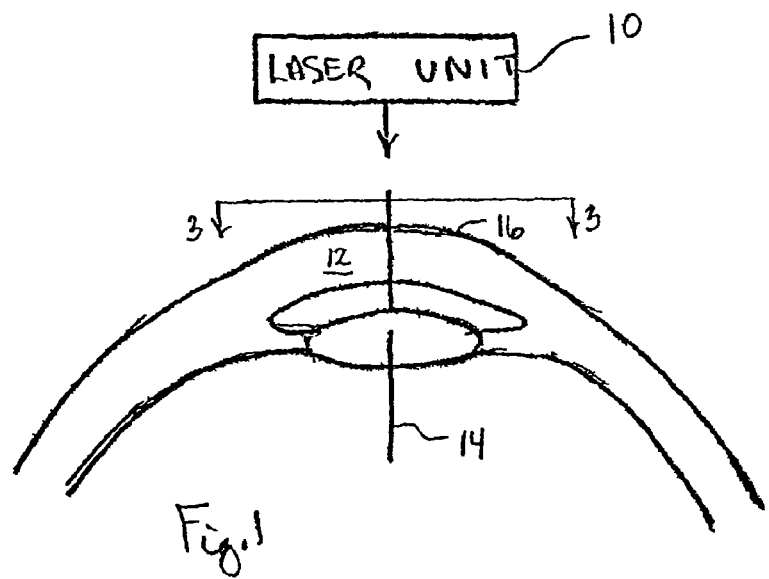
FIG. 1 is a cross section view of the cornea of an eye, shown with a laser unit positioned for incising stromal tissue in the cornea in accordance with the present invention.

Referring initially to FIG. 1 a laser unit for use with the present invention is shown and is designated 10. Preferably, the laser unit 10 is of a type well known in the pertinent art for generating a pulsed femtosecond laser beam that is capable of performing Laser Induced Optical Breakdown (LIOB) on stromal tissue in a cornea 12. As shown, the cornea 12 defines a visual axis 14, and it has an anterior surface 16.

Figure 2A:
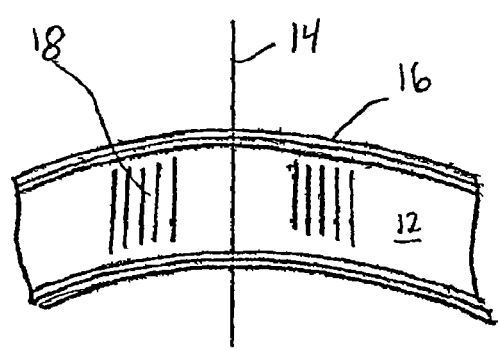
FIG. 2A is a cross section view of the cornea of FIG. 1 shown with regular incisions introduced into the stroma to weaken the stroma for correcting a vision defect of the eye.
Figure 2B:
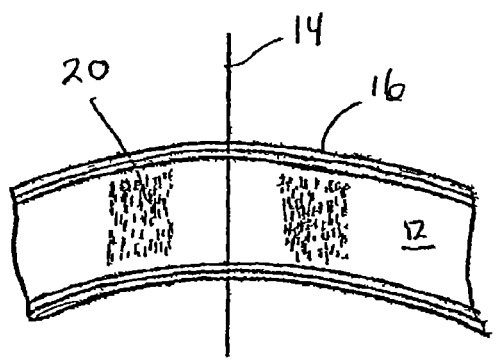
FIG. 2B is a view of the cornea of FIG. 1 shown with irregular incisions, rather than regular incisions as shown in FIG. 2A.

In overview, the laser unit 10 is used to weaken stromal tissue in the cornea 12 for the purpose of providing a refractive correction. Specifically, FIG. 2A shows a pattern 18 of regular incisions in the cornea 12 made for this purpose. More specifically, the pattern 18 will typically have a plurality of concentric cylindrical incisions that are centered on the visual axis 14. The procedure and consequence of creating the pattern 18 of regular incisions is fully disclosed in the co-pending '202 Appln. mentioned above. Similarly, FIG. 2B shows the presentation of a pattern 20 of irregular incisions as intended for the present invention. In detail, the pattern 20 is a pseudo-random pattern wherein dimensions and locations of incisions within the pattern 20 are based on a statistical distribution that is generated by a random number generator (not shown). Although both the pattern 18 and the pattern 20 are selected to achieve a same refractive correction for cornea 12, the pattern 20 is specifically intended to do so while minimizing any adverse side effects that might otherwise result.

Figure 3:
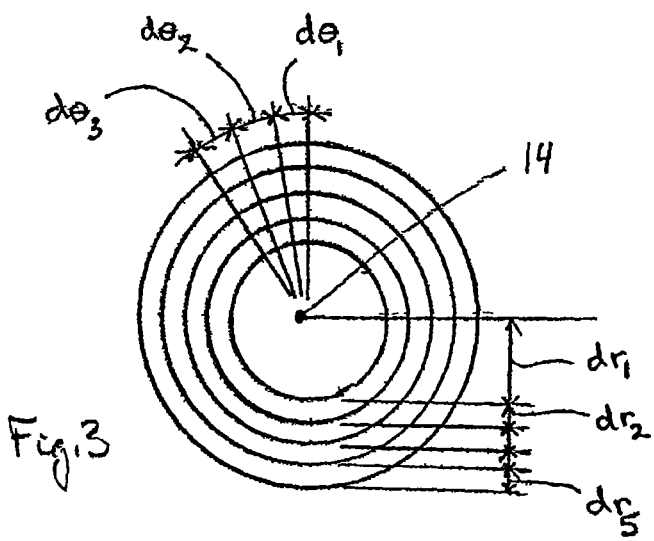
FIG. 3 is a top plan view of geometrical properties for incisions contemplated for the present invention as would be seen in the entire cornea along the line 3-3 in FIG. 1.
Figure 4:
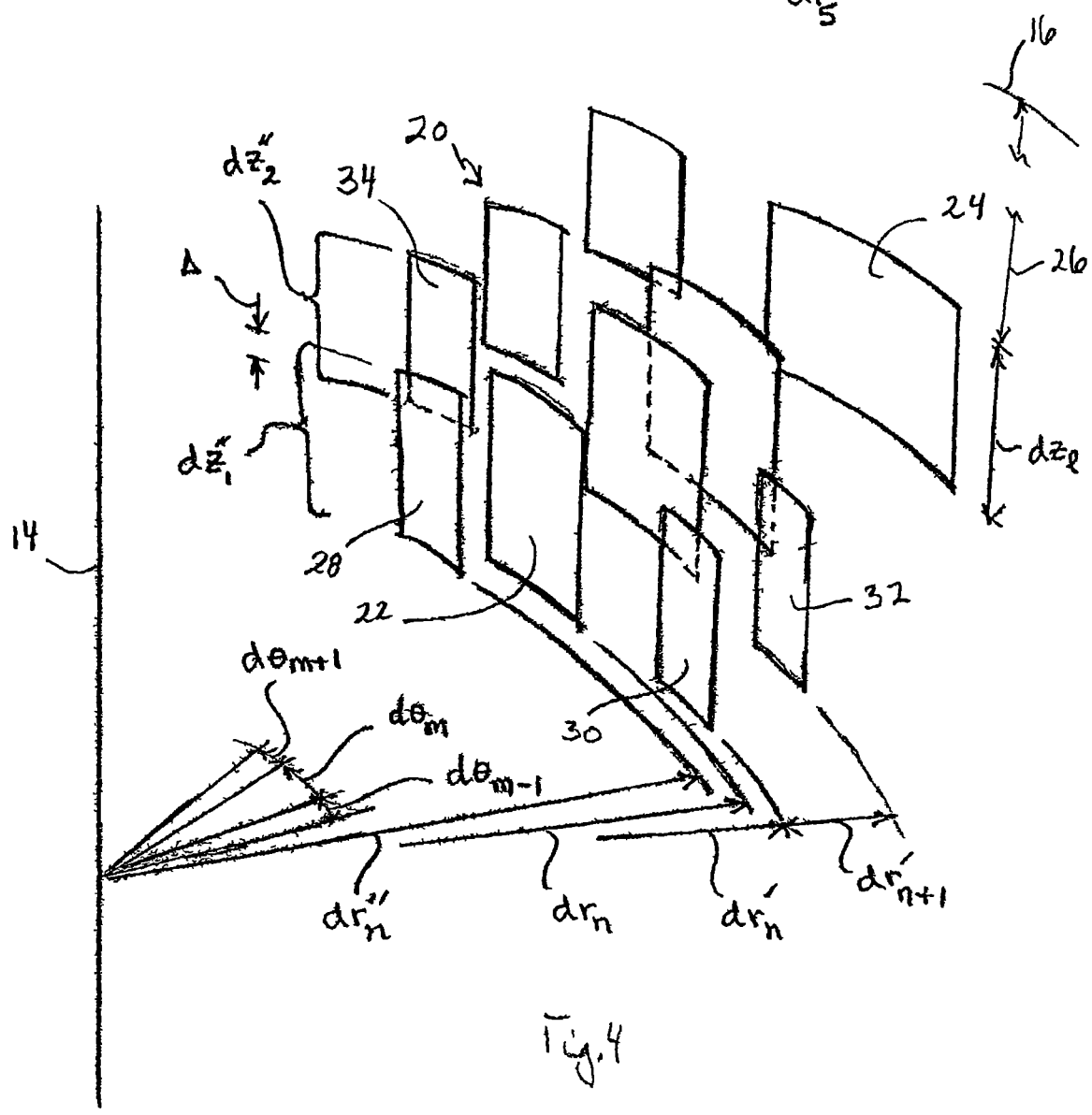
FIG. 4 is a perspective view of a plurality of irregular incisions located inside the stroma of an eye, shown relative to the visual axis of an eye in accordance with the present invention.
Figure 3:
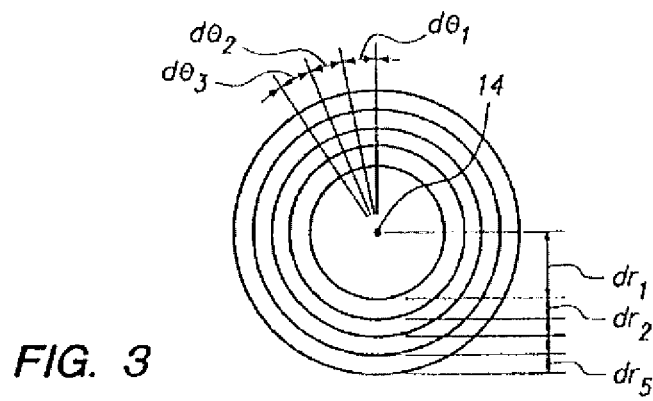
Figure 4:
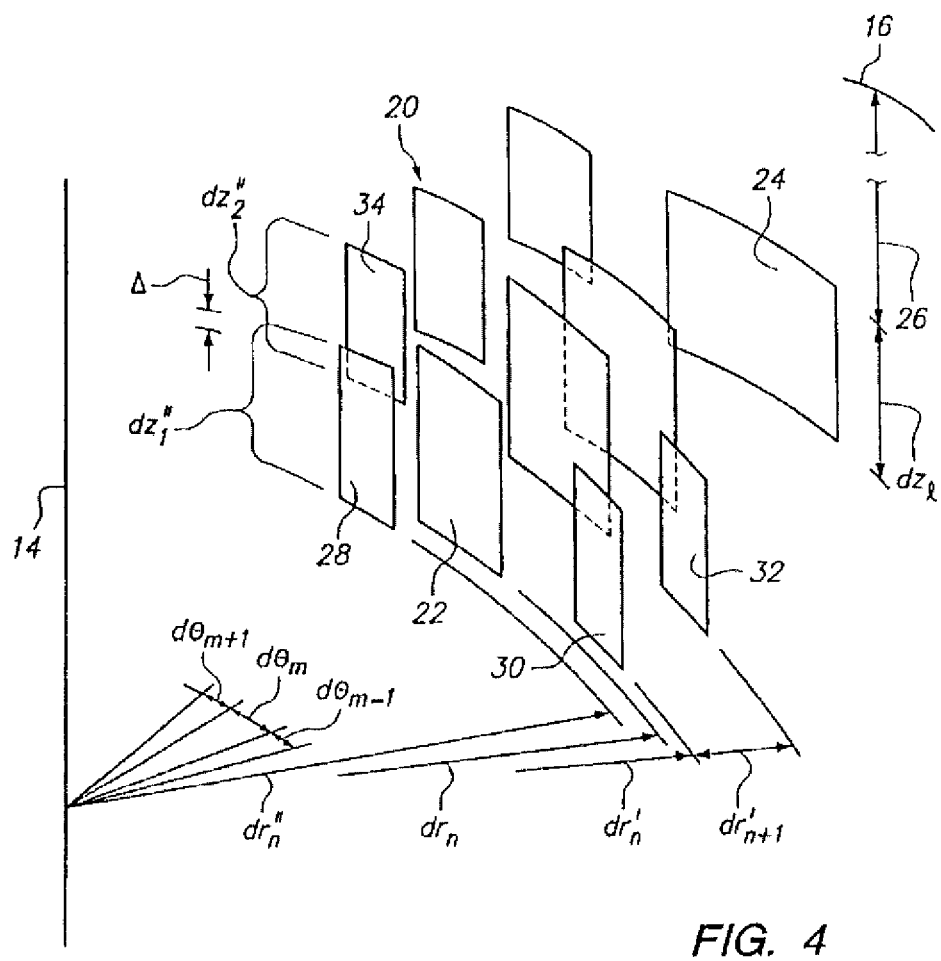

With the above in mind, creation of the pattern 20 will be best appreciated by cross referencing FIG. 3 with FIG. 4. To begin, and with initial reference to FIG. 4, it is to be noted that the pattern 20 includes a plurality of irregular incisions, of which the irregular incision 22 is exemplary. Dimensionally, the irregular incision 22 is defined by an arc width "$dθ_m$" and by a length "$dz_I$". Further, it is also to be noted that the location of the irregular incision 22 is established within its arc width dθ by a characteristic radial distance increment "$dr_n$". With reference to FIG. 3, it can be seen that the radial distance $dr_n$ (e.g. of incision 22) is measured along a radial line extending outwardly from the visual axis 14. Further, with reference back to FIG. 4, it will be seen that the length dz (e.g. of incision 24) is measured along a line 26 that is substantially perpendicular to the anterior surface 16 of the cornea 12 and substantially parallel to the visual axis 14. In this context, all irregular incisions having the same arc width $dθ_m$ (e.g. m=1), and being in the same level (e.g. I=1 for length $dz_1$), such as the irregular incisions 22 and 24, will also have a substantially same length $dz_1$.

Dimensional parameters for the irregular incision 22 shown in FIG. 4, as for all other incisions in pattern 20, are selected within predetermined ranges. For example, the arc width $dθ_m$ for the irregular incision 22 and for the irregular incision 24 is the same, and is in a range between approximately 8° and 12°. Preferably, m=1→36, and $Σdθ_m$=360°. Further, all incisions in a same level "I" and having a same $dθ_m$, will also have a same length $dz_I$. Preferably, I=1→10 (i.e. there are ten levels), with each $dz_I$ being in a range of 30 μm to 50 μm. As envisioned for the present invention an overlap "Δ" can be selectively added to the length dz to contribute to the continuity of the pattern 20. If added, Δ will be preferably less than approximately 10 μm. Also, the irregular incisions (e.g. incisions 22 and 24) having a same $dθ_m$ are each located in the $dθ_m$ by a characteristic incremental radial distance $dr_n$. In general, n=1→5, $dr_1$>1 mm and $Σdr_n$<approximately 2 mm. As envisioned for the present invention, values for $dθ_m$, $dz_I$ and $dr_n$ are established by using a random number generator (not shown).

With the above in mind, and by way of example, consider the relative dimensions and locations of the irregular incisions 22, 28, 30, 32 and 34 shown in FIG. 4. First, however, consider only the irregular incisions 22, 28, and 30. In this example, the incisions 22, 28 and 30 are located in the same level (i.e. I=1), but they are in respectively different arcs (i.e. they each have a different $dθ_m$). Thus, for m=2, the irregular incision 30 is located in the arc $dθ_1$, the irregular incision 22 is located in the arc $dθ_2$, and the irregular incision 28 is located in the arc $dθ_3$. At this point it is to be noted that each of the incisions 22, 28 and 30 also have a different characteristic radial increment $dr_n$. Specifically, for n=1, the irregular incision 22 has a radial distance increment $dr_1$, the irregular incision 30 has a radial distance increment $dr'_1$, and the irregular incision 28 has a radial distance increment $dr''_1$. To ensure continued biomechanical efficiency, the differences between radial distance increments $dr_1$, $dr'_1$, and $d''r_1$ for the respective irregular incisions 22, 30 and 28 are established to be within a predetermined radial distance of each other. Preferably, this distance is not greater than about 20 microns.

For another aspect of the pattern 20, consider the irregular incisions that are in the same arc $dθ_1$ (e.g. incisions 30 and 32). In this case (i.e. same $d\theta_m$), in order to avoid adverse LIOB consequences, the distance between irregular incisions with different radial distance increments $dr_n$ (e.g. n=1 for incision 30; and n=2 for incision 32) is preferably greater than approximately 50 μm. In this example, $dr'_1$ for irregular incision 30 will preferably be about 1 mm and $dr'_2$ for the irregular incision 32 will be greater than 50 μm. Note, as used herein the radial distance increments $dr_n$ are additive. Thus, stated differently, irregular incision 30 is approximately 1 mm radial distance from the visual axis 14, and the irregular incision 32 will be at least 1.05 mm distance from the visual axis 14.

Finally, consider irregular incisions that have the same arc width $d\theta_m$, but are in different levels. For example, refer to the irregular incisions 28 and 34 in FIG. 4. They both have the same arc $d\theta_3$ but they are at different levels (i.e. I=1 for incision 28; and I=2 for incision 34). They may also have different lengths $dz_l$ and, importantly, they must have different radial distance increments $dr_n$. Indeed, by having different radial distances $dr_n$ there can be an overlap Δ established between the irregular incisions 28 and 34.

In preparation for an actual surgical procedure, the desired optical correction must first be diagnosed and defined. Then, an appropriate change in the biomechanical stress distribution within the stroma that will result in the desired optical correction must be defined. With this information, the variable parameters dθ, dz, dr, and Δ as discussed above are statistically determined by a random number generator to establish the pattern 20.

While the particular Minimizing the Side-Effects of Refractive Corrections Using Statistically Determined Irregularities in Intrastromal Incisions as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

GLOSSARY-FILE #11270.86 laser unit 52
cornea 54
visual axis 56
anterior surface 58
pattern (regular incision) 60
pattern (irregular incision) 62
irregular incision 64
irregular incision 66
line 68
irregular incision 70
irregular incision 72
irregular incision 74
irregular incision 76
78
80
82
dθ arc width
dz length
dr radial distance

What is claimed is:

1. A method for minimizing visual side-effects of a refractive surgical procedure which comprises the steps of:
   identifying a change for biomechanical stresses within a stroma of an eye, wherein the change is necessary to affect a defined optical correction;
   determining a statistical distribution for structural alterations in the stroma to implement the change;
   creating a plurality of unique irregular incisions manifesting the structural alterations in the stroma to accomplish the optical correction;
   locating each irregular incision in accordance with the statistical distribution to cause the plurality of irregular incisions to become visually elusive for minimizing the visual side-effects of the surgical procedure while achieving the defined optical correction; and
   wherein the eye defines a visual axis and has an anterior surface, and wherein each irregular incision is defined by a length $dz_l$ measured along a line perpendicular to the anterior surface and by an arc width $d\theta_m$ measured along an azimuthal arc centered on the visual axis, and further wherein each irregular incision is located at a radial distance $dr_n$ from the visual axis.

2. A method as recited in claim 1 wherein each arc width $d\theta_m$ is in a range between approximately 8° and 12°, wherein m =1→36, and wherein $\Sigma d\theta_m$ =360°.

3. A method as recited in claim 2 wherein each irregular incision having a same $d\theta_m$ has a same $dz_l$ +an overlap Δ, wherein l=1→10, wherein each $dz_l$ is in a range of 30 μm to 50 μm, and further wherein Δ<approximately 10 μm.

4. A method as recited in claim 3 wherein each irregular incision having a same $d\theta_m$ is located by said radial distance $dr_n$, wherein n=1→5, $dr_1$ >1 mm and $\Sigma dr_n$ <approximately 2 mm.

5. A method as recited in claim 4 wherein the distance $dr_n$ for an irregular incision in a $d\theta_m$ is established to be within a respective predetermined radial distance of other irregular incisions with a same $dr_n$ in $d\theta_{m+1}$ and in $d\theta_{m-1}$.

6. A method as recited in claim 4 wherein the distance between $dr_n$ and $dr_{n+1}$ within a same $d\theta_m$ is greater than approximately 50 μm.

7. A method as recited in claim 4 wherein values for $d\theta_m$, $dz_l$ and $dr_n$ are established by using a random number generator.

8. A method as recited in claim 4 wherein $dr_n$ is a radial extension of $dr_{n+1}$.

9. A method as recited in claim 1 wherein the irregular incisions of $d\theta_m$ are axially symmetric with the irregular incision of $d\theta_m$ +180°.

10. A method for creating a pattern of irregular incisions in the stroma of an eye to correct a vision defect, with minimal resulting visual side effects, the method comprising the steps of:
    defining each irregular incision in the pattern relative to a geometry of the eye, wherein the eye geometry includes a visual axis and an anterior surface, and each irregular incision has an arc width $d\theta_m$ measured along an azimuthal arc centered on the visual axis, with a length $dz_l$ plus an overlap Δ measured along a line substantially perpendicular to the anterior surface of the eye;
    locating each irregular incision within a same $d\theta_m$ using a characteristic radial distance $dr_n$; and
    using a random number generator to establish values for $d\theta_m$, $dz_l$ and $dr_n$.

11. A method as recited in claim 10 wherein each arc width $d\theta_m$ is in a range between approximately 8° and 12°, where m =1→36 and $\Sigma d\theta_m$=360°, wherein l=1→10 and each $dz_l$ is in a range of 30 μm to 50 μm with Δ less than approximately 10 μm, and further wherein n =1→5 with $dr_1$ greater than approximately 1 mm and $\Sigma dr_n$ less than approximately 2 mm.

12. A method as recited in claim 10 wherein $dr_n$ and $dz_l$ of $d\theta_m$ is the same as the respective $dr_n$ and $dz_l$ of $d\theta_m+180°$.

13. A method as recited in claim 12 wherein $m=1\rightarrow 18$ and $\Sigma d\theta_m=180°$.

14. A method as recited in claim 10 wherein the distance $dr_n$ for an irregular incision in a $d\theta_m$ is established to be within a respective predetermined radial distance of other irregular incisions with a same $dr_n$ in $d\theta_{m+1}$ and in $d\theta_{m-1}$.

15. A method as recited in claim 14 wherein the distance between $dr_n$ and $dr_{n+1}$ within a same $d\theta_m$ is greater than approximately 50 µm.

\* \* \* \* \*

UNITED STATES PATENT AND TRADEMARK OFFICE
CERTIFICATE OF CORRECTION

Page 1 of 5

PATENT NO.         : 8,377,048 B2
APPLICATION NO.    : 12/349257
DATED              : February 19, 2013
INVENTOR(S)        : Josef F. Bille It is certified that error appears in the above-identified patent and that said Letters Patent is hereby corrected as shown below:

Delete the title page and substitute therefore with the attached title page consisting of the corrected illustrative figures.

In the Drawings

Delete Drawing Sheets 1-2 and substitute therefore with the attached Drawing Sheets 1-2.

In the Specification

Column 2, Line 3 - DELETE "illusive" and INSERT -- elusive --;

Column 3, Line 1 - DELETE "uppercase I=1" and INSERT -- l = 1 --;

Column 4, Line 24 - DELETE "uppercase I=1" and INSERT -- l = 1 --;

Column 4, Line 33 - DELETE "uppercase "I" and INSERT -- lowercase "l" --;

Column 4, Line 34 - DELETE "uppercase I=1" and INSERT -- l = 1 --;

Column 4, Line 51 - DELETE "uppercase I=1" and INSERT -- l = 1 --;

Column 5, Line 15 - DELETE "uppercase I=1" and INSERT -- l = 1 --;

Column 5, Line 16 - DELETE "I=2" and INSERT -- l = 2 --;

Signed and Sealed this
Twenty-fifth Day of February, 2014

Michelle K. Lee
*Deputy Director of the United States Patent and Trademark Office*

CERTIFICATE OF CORRECTION (continued)
U.S. Pat. No. 8,377,048 B2

Column 5, Line 38 to Line 59 - DELETE the GLOSSARY-FILE #11270.86 in its entirety;

Column 6, Line 22 - DELETE "+an" and INSERT -- + an --.

Column 1, Line 41 - to Column 2, Line 13 INSERT periods as shown below:

A recently presented procedure for introducing refractive corrections (e.g. the correction of presbyopia) into the cornea of an eye, without LASIK, involves the weakening of tissue in the stroma. Specifically, such a procedure is disclosed in U.S. Pat. Appln. Ser. No. 11/958,202 for an invention entitled "Method for Intrastromal Refractive Surgery," (hereinafter the "'202 Appln.") which is assigned to the same assignee as the present invention. As disclosed in the '202 Appln., the weakening of stromal tissue is accomplished using a pulsed femtosecond laser beam to create incisions in the stroma. It can happen in a small number of cases, however, that these incisions may introduce annoying side-effects in night-vision (e.g. Halos, ring-patterns around bright light sources). Further, annoying side-effects may result inherently due to the multifocality of the reshaped cornea. In any event, the unwanted side-effects are preferably overcome via neuro-adaptive suppression.

In one of its aspects, neuro-adaptive suppression involves having the brain effectively ignore a visual perception. For example, it can be demonstrated that a plethora of irregularities (e.g. stromal incisions) may be presented in a manner that will visually disguise an underlying regularity. Insofar as an ophthalmic laser procedure is concerned, such a neuro-adaptive suppression may be very advantageous. In particular, this will be so if the collective irregularities simultaneously accomplish a two-fold purpose. For one, a pattern of collective irregularities must accomplish the same refractive correction that would otherwise be obtained by the underlying regularity alone. For another, the pattern of irregularities needs to be visually elusive (i.e. obfuscate the underlying regularity), and thereby minimize any annoying visual side-effects (e.g. Halos) that might otherwise arise.

In light of the above, it is an object of the present invention to provide a system and method for minimizing visual side-effects of a refractive surgical procedure that achieves a desired refractive correction with a pseudo-random pattern of irregular stromal incisions. Another object of the present invention is to create a pseudo-random pattern of irregular stromal incisions, based on a statistical distribution, for correcting a vision defect with minimal residual side-effects. Still

(12) United States Patent
Bille

(10) Patent No.: US 8,377,048 B2
(45) Date of Patent: Feb. 19, 2013

(54) MINIMIZING THE SIDE-EFFECTS OF REFRACTIVE CORRECTIONS USING STATISTICALLY DETERMINED IRREGULARITIES IN INTRASTROMAL INCISIONS

(75) Inventor: Josef F. Bille, Heidelberg (DE)

(73) Assignee: Technolas Perfect Vision GmbH, Munich (DE)

(*) Notice: Subject to any disclaimer, the term of this patent is extended or adjusted under 35 U.S.C. 154(b) by 1081 days.

(21) Appl. No.: 12/349,257

(22) Filed: Jan. 6, 2009

(65) Prior Publication Data

US 2010/0174274 A1 Jul. 8, 2010

(51) Int. Cl.
*A61B 18/18* (2006.01)
(52) U.S. Cl. .................................................. 606/5
(58) Field of Classification Search ............ 128/898; 606/4–6; 623/4.1–6.64, 905–907
See application file for complete search history.

(56) References Cited

U.S. PATENT DOCUMENTS

| | | | |
|---|---|---|---|
| 4,309,998 A | 1/1982 | Aron nee Rosa et al. | |
| 4,391,275 A | 7/1983 | Fankhauser et al. | |
| 4,669,466 A | 6/1987 | L'Esperance | |
| 4,718,418 A | 1/1988 | L'Esperance, Jr. | |
| 4,721,379 A | 1/1988 | L'Esperance | |
| 4,732,148 A | 3/1988 | L'Esperance, Jr. | |
| 4,770,172 A | 9/1988 | L'Esperance, Jr. | |
| 4,887,592 A | 12/1989 | Loertscher | |
| 4,907,586 A | 3/1990 | Bille et al. | |
| 4,941,093 A | 7/1990 | Marshall et al. | |
| 4,988,348 A | 1/1991 | Bille | |
| 5,549,632 A | 8/1996 | Lai | |
| 5,984,916 A | 11/1999 | Lai | |
| 5,993,438 A | 11/1999 | Juhasz et al. | |
| 6,110,166 A | 8/2000 | Juhasz | |
| 6,325,792 B1 | 12/2001 | Swinger et al. | |
| 6,610,051 B2 | 8/2003 | Bille | |
| 6,648,877 B1* | 11/2003 | Juhasz et al. | 606/5 |
| 2004/0044355 A1 | 3/2004 | Nevyas | |
| 2006/0106372 A1* | 5/2006 | Kuhn et al. | 606/5 |
| 2008/0039825 A1* | 2/2008 | Lai | 606/5 |
| 2008/0306573 A1* | 12/2008 | Campin et al. | 607/89 |
| 2008/0319464 A1 | 12/2008 | Bischoff et al. | |

* cited by examiner

*Primary Examiner* — Ryan Severson
*Assistant Examiner* — David Eastwood
(74) *Attorney, Agent, or Firm* — Nydegger & Associates

(57) ABSTRACT

A system and method for minimizing adverse visual effects that may be introduced during laser refractive surgery, requires making laser incisions into stromal tissue in a predetermined manner. Specifically, a plurality of irregular incisions are statistically distributed in the stroma in a manner that causes them to be visually elusive, and thereby minimize their adverse visual effects. The incisions must, however, still accomplish their intended surgical purpose of weakening the stroma in a predetermined manner. To do this, each irregular incision has a width of arc length $d0_m$, a length $dz_l$ and a characteristic radial distance $dr_n$ from the visual axis of the eye. Values for $d0_m$, $dz_l$ and $dr_n$ are established using a random number generator.

15 Claims, 2 Drawing Sheets

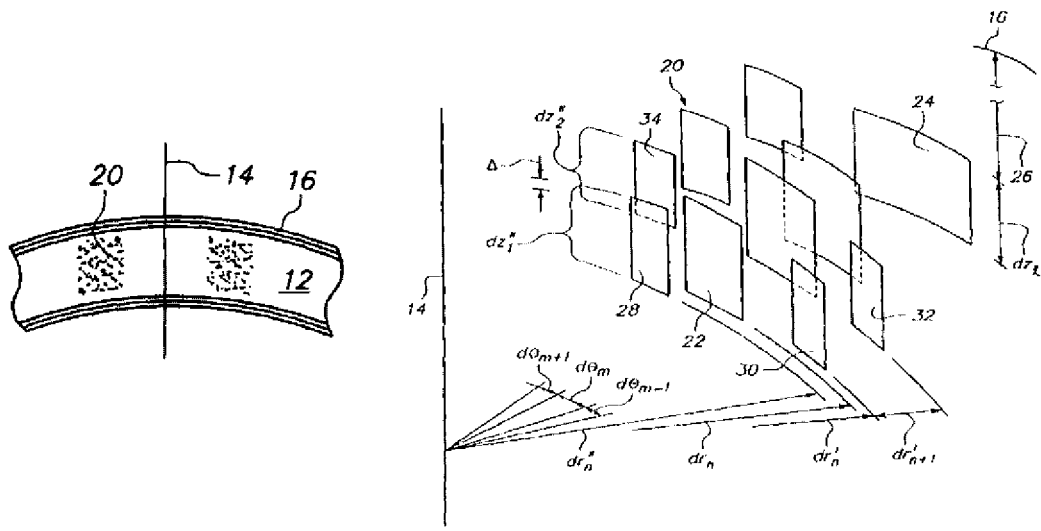

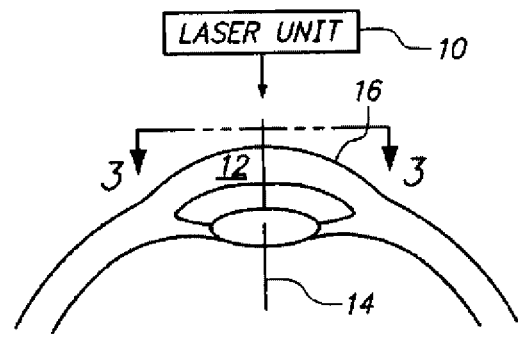
FIG. 1
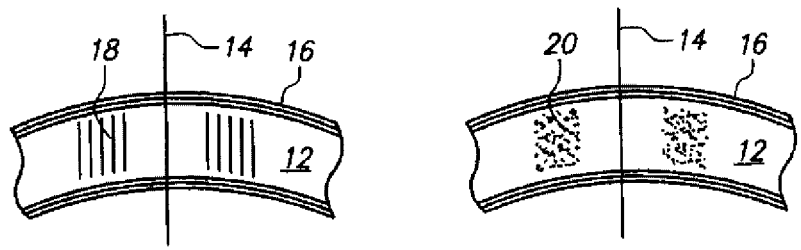
FIG. 2A  FIG. 2B